(12) United States Patent
Hsiung et al.

(10) Patent No.: US 11,464,936 B2
(45) Date of Patent: Oct. 11, 2022

(54) AUTO FEED HUMIDIFICATION CHAMBER WITH IMPROVED STRUCTURE

(71) Applicant: BESMED HEALTH BUSINESS CORP., New Taipei (TW)

(72) Inventors: Tao-Tsun Hsiung, New Taipei (TW); Xu-Xiang Wang, New Taipei (TW); I-Chen Tsai, New Taipei (TW)

(73) Assignee: BESMED HEALTH BUSINESS CORP., New Taipei (TW)

( * ) Notice: Subject to any disclaimer, the term of this patent is extended or adjusted under 35 U.S.C. 154(b) by 222 days.

(21) Appl. No.: 16/657,314

(22) Filed: Oct. 18, 2019

(65) Prior Publication Data

US 2020/0338300 A1 Oct. 29, 2020

(30) Foreign Application Priority Data

Apr. 25, 2019 (TW) .................................. 108114835
Apr. 25, 2019 (TW) .................................. 108205245

(51) Int. Cl.
 *A61M 16/16* (2006.01)
(52) U.S. Cl.
 CPC .................................. *A61M 16/167* (2014.02)
(58) Field of Classification Search
 CPC .............. A61M 16/16–168; A61M 16/20–209
 See application file for complete search history.

(56) References Cited

U.S. PATENT DOCUMENTS

| | | | | |
|---|---|---|---|---|
| 4,201,204 A * | 5/1980 | Rinne | ................. | A61M 16/109 128/203.27 |
| 4,225,542 A * | 9/1980 | Wall | ................. | A61M 16/1075 128/203.12 |
| 5,943,473 A * | 8/1999 | Levine | ................. | A61M 16/167 392/401 |
| 2004/0040599 A1* | 3/2004 | Payne | ................. | B29C 44/0415 137/409 |
| 2008/0054500 A1* | 3/2008 | Bradley | ............. | A61M 16/167 261/70 |
| 2010/0171229 A1* | 7/2010 | Payne | ................. | A61M 16/167 261/4 |

(Continued)

*Primary Examiner* — Valerie L Woodward
(74) *Attorney, Agent, or Firm* — Bacon & Thomas, PLLC

(57) ABSTRACT

An auto feed humidification chamber with improved structure, the humidification chamber comprises a shell body, an extending tube, a float, a sealing element and a heated plate; the inside of the shell body is provided with a plurality of passage spacer plates, the extending tube is integrally formed on the inside of the shell body, the extending tube has a plurality of positioning blocks; the float is a hollow container, the central portion of the float has an extending portion, a top end of the extending portion has a plurality of hooks, the sealing element can be disposed on the top end of the extending portion; the heated plate is located below the shell body, and the heated plate is used for sealing the shell body to form a chamber space; wherein the extending portion can be suspended on the extending tube by the plurality hooks and the plurality positioning blocks, the passage spacer plates and the concave portions form at least two complicated gas passages in the chamber space, the outside surface of the float and the wall surface of the shell body form at least two annular gas passages in the chamber space.

16 Claims, 15 Drawing Sheets

(56) References Cited

U.S. PATENT DOCUMENTS

2011/0108028 A1\* 5/2011 Zollinger ............ A61M 16/167
                                                    128/203.12
2011/0156289 A1\* 6/2011 Steg ...................... A61M 16/16
                                                    261/70

\* cited by examiner

AUTO FEED HUMIDIFICATION CHAMBER WITH IMPROVED STRUCTURE

BACKGROUND OF THE INVENTION

1. Field of the Invention

The present invention relates to a humidification chamber and more particularly to an auto feed humidification chamber with improved structure, wherein a float is disposed in the humidification chamber, and the float is suspended on a shell body of the humidification chamber, therefore a bottom of the float will not contact with a heated plate of the humidification chamber. During the humidification process, the humidification chamber can be replenished a liquid, the float can rise and fall with the water level of the humidification chamber. When a water inlet of the humidification chamber is blocked by the float, the liquid replenishment of the humidification chamber can be stopped to control the water level of the humidification chamber.

2. Description of Related Art

A first prior-art is US Patent Application Publication No. US20160199614, the first prior-art disclosed a float retention arrangement for humidification chamber, a primary float (116) is connected to a coupling arm (118), the primary float (116) moves a push rod (124) by the coupling arm (118) so as to actuate a primary valve (112). The push rod (124) includes a lower end portion (128) pivotally coupled to the coupling arm (118) and an upper end portion (126). The upper end portion (126) includes a valve body (130), the valve body (130) can engage the first valve seat (132), directly or indirectly, to close the primary valve (112), and prevents water entering the humidification chamber (100) via the primary valve (112). The valve body (130) can also be disengaged from the first valve seat (132) to open the primary valve (112) and permit entry of water into the humidification chamber (100). One end of the supply tube (150) is coupled to the water inlet (108) and the other end of the supply tube (150) is coupled to an adapter for coupling the supply tube (150) to a source of water. The adapter can be in the form of a water spike (152), the water spike (152) can also be used as a retention device of the primary float (116). The first prior-art is not easy to assemble, and the cost of first prior-art is higher. Thus, the first prior-art still requires improvement.

A second prior-art is disclosed in U.S. Pat. No. 7,722,016, the prior-art disclosed a humidification chamber, the humidification chamber has a float, the float has a seal element which is movable into and out of a valve seat; when the water level of the humidification chamber exceeds a first level, the seal element will seal off a water inlet; when the water level of the humidification chamber is below the first level, the seal element will open the water inlet; the float has a stand-off rib (94) to prevent the lower end of the float from contacting a heat conductive plate. The stand-off rib (94) of the float may still be in contact with the heat conductive plate when the water level of the humidification chamber is too low. Moreover, the stand-off rib (94) of the float may still be in contact with the heat conductive plate when the water inlet does not replenish water into the humidification chamber (e.g., a water storage container connected to the water inlet has no water). Thus, the second prior-art still requires improvement.

SUMMARY OF THE INVENTION

It is therefore an object of the invention to provide an auto feed humidification chamber with improved structure, the humidification chamber comprises a shell body, an extending tube, a float, a sealing element and a heated plate; the inside of the shell body is provided with a plurality of passage spacer plates, the extending tube is integrally formed on the inside of the shell body, the extending tube has a plurality of positioning blocks; the float is a hollow container, the central portion of the float has an extending portion, a top end of the extending portion has a plurality of hooks, the sealing element can be disposed on the top end of the extending portion; the heated plate is located below the shell body, and the heated plate is used for sealing the shell body to form a chamber space; wherein the extending portion can be suspended on the extending tube by the plurality hooks and the plurality positioning blocks, the passage spacer plates and the concave portions form at least two complicated gas passages in the chamber space, the outside surface of the float and the wall surface of the shell body form at least two annular gas passages in the chamber space.

It is therefore another object of the invention to provide an auto feed humidification chamber with improved structure, the humidification chamber has a float which is a hollow container, the float comprises an extending portion, a plurality of hooks, a plurality of concave portions and a sealing element; the extending portion is disposed at the central portion of the float, the plurality hooks are disposed at a top end of the extending portion, the plurality concave portions are annularly disposed on the extending portion, the sealing element can be fixed on the top end of the extending portion; wherein the float can be suspended in a chamber space of the humidification chamber by the hooks, the plurality concave portions can form at least two complicated gas passages in the chamber space, the outside surface of the float can form at least two annular gas passages in the chamber space.

First advantages of the invention include the extending portion of the float is directly combined to the extending tube of the shell body, the extending portion is directly suspended on the extending tube. Namely, the extending tube of the shell body can be served as a retaining device for the float, therefore a distance can be formed between the heated plate and the bottom of the float. Thus, the invention is easy to assemble, and the cost of the invention can be reduced.

Second advantages of the invention include the complicated gas passages can increase the residence time of a gas when the gas enters the chamber space, the annular gas passages can guide the moisture in the chamber space, and therefore the gas will mix well with the moisture.

Third advantages of the invention include the plurality concave portions are symmetrically disposed on the float, the plurality passage spacer plates are symmetrically disposed in the shell body, and therefore the assembly of the float and the shell body is provided with a foolproof effect; as a result of the assembly of the float and the shell body has the foolproof effect, a gas inlet and a gas outlet of the shell body are also provided with a foolproof effect. Namely, the gas inlet and the gas outlet can be interchangeable to use, the user does not need to identify the gas inlet and the gas outlet.

The above and other objects, features and advantages of the invention will become apparent from the following detailed description taken with the accompanying drawings.

DETAILED DESCRIPTION OF THE INVENTION

Figure 10:
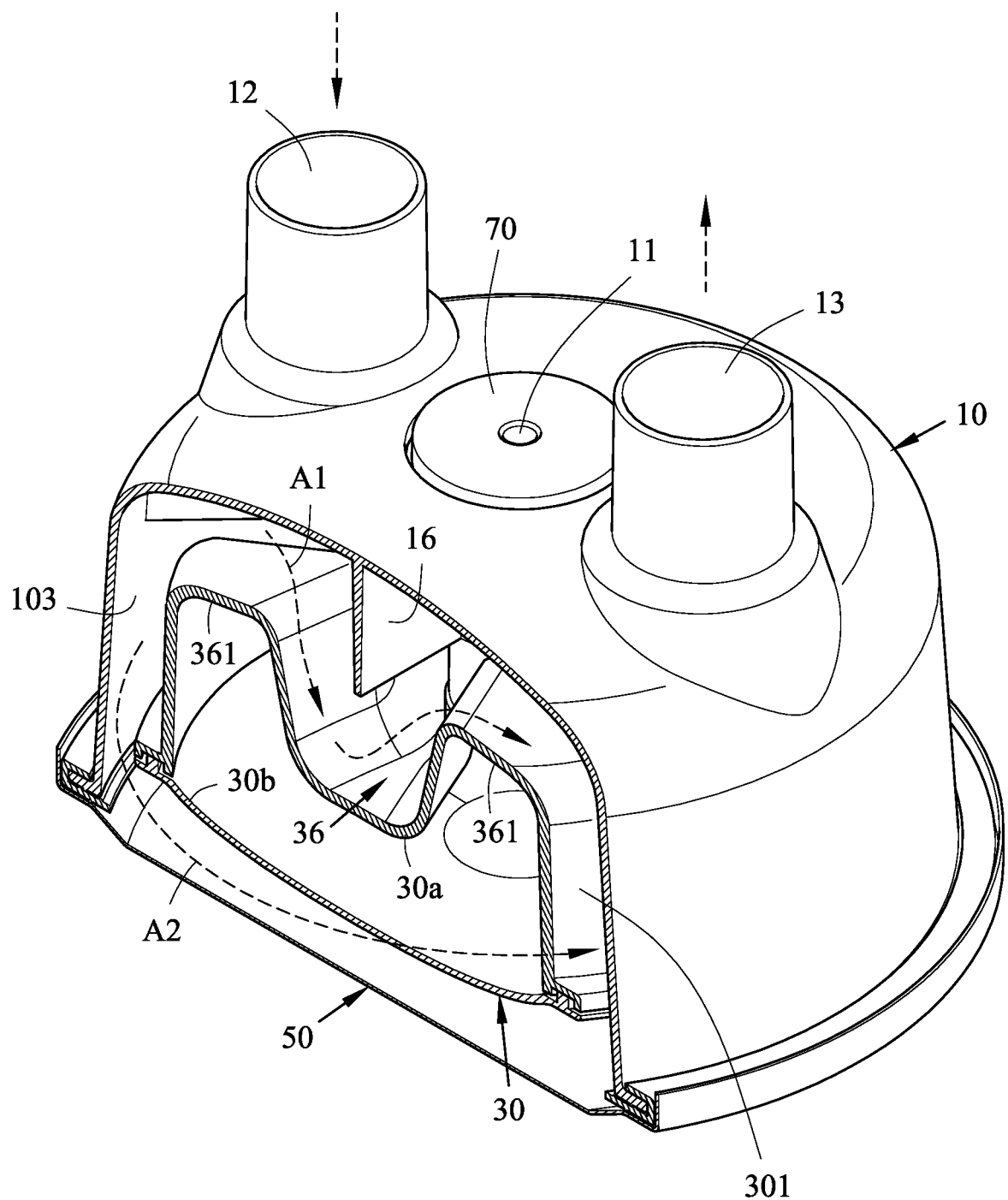
FIG. 10 is a cross-sectional perspective view along a line A-A of FIG. 1.
Figure 11:
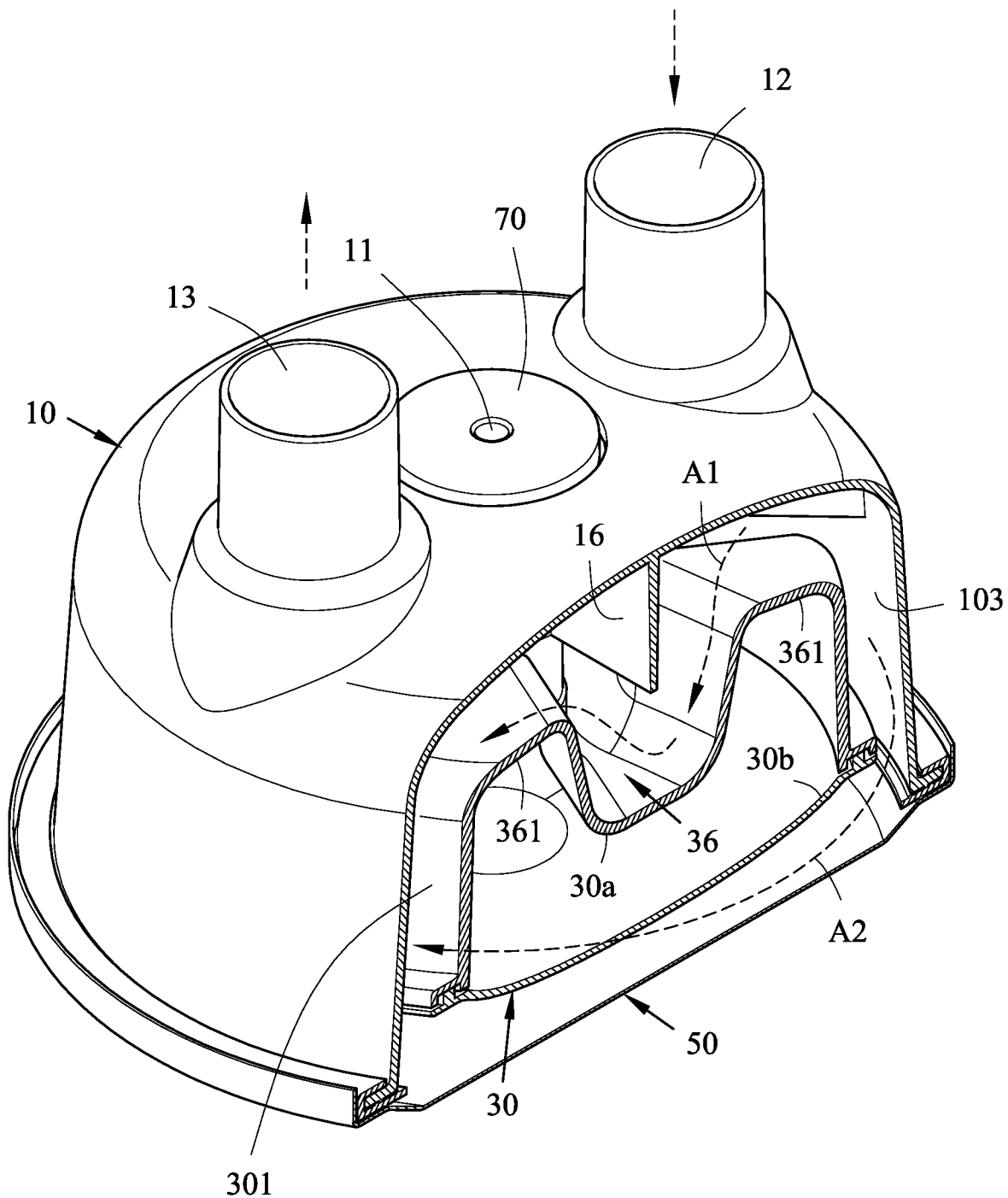
FIG. 11 is a cross-sectional perspective view along a line B-B of FIG. 1.
Figure 12:
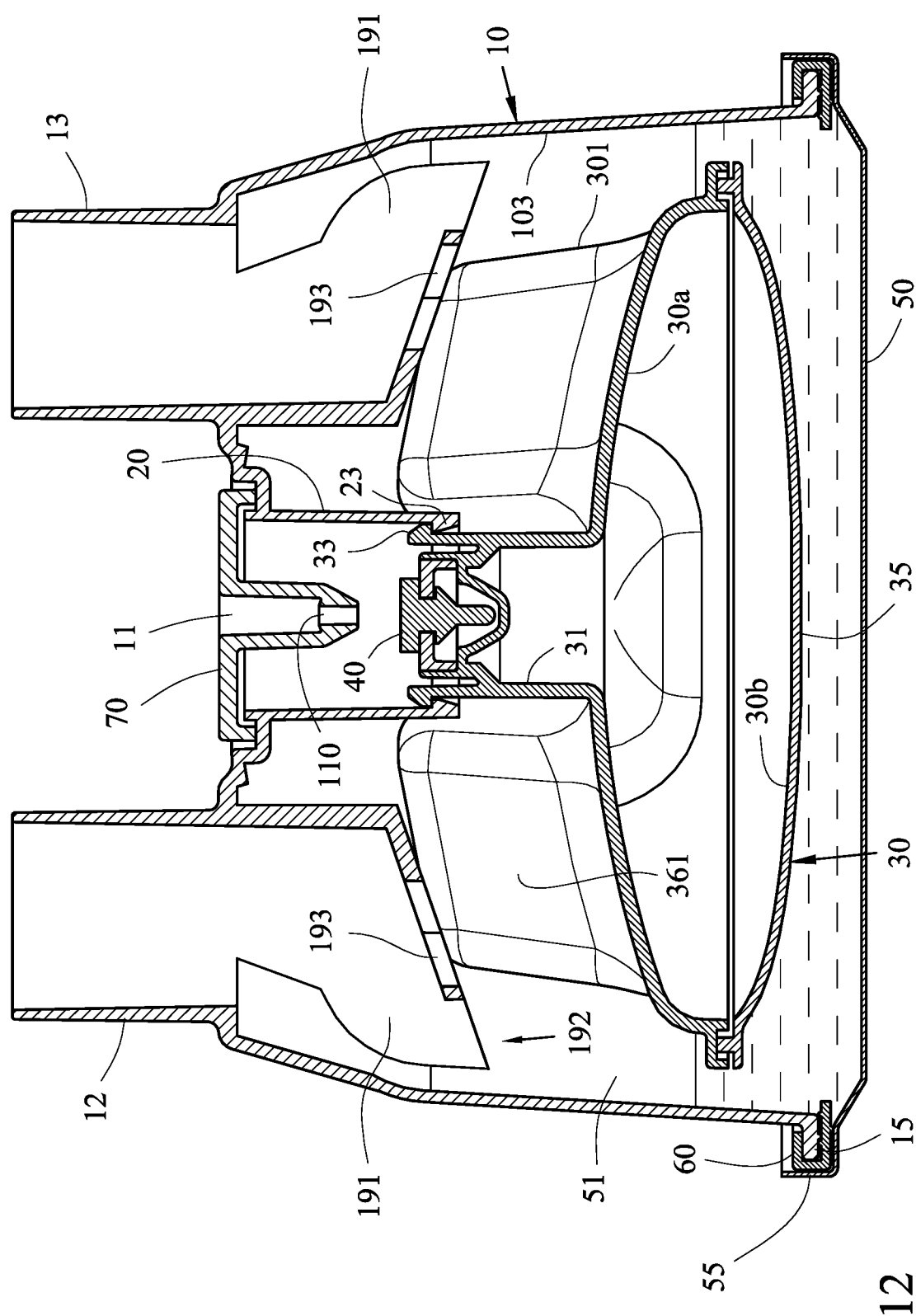
FIG. 12 is a cross-sectional view along a line C-C of FIG. 1.
Figure 14:
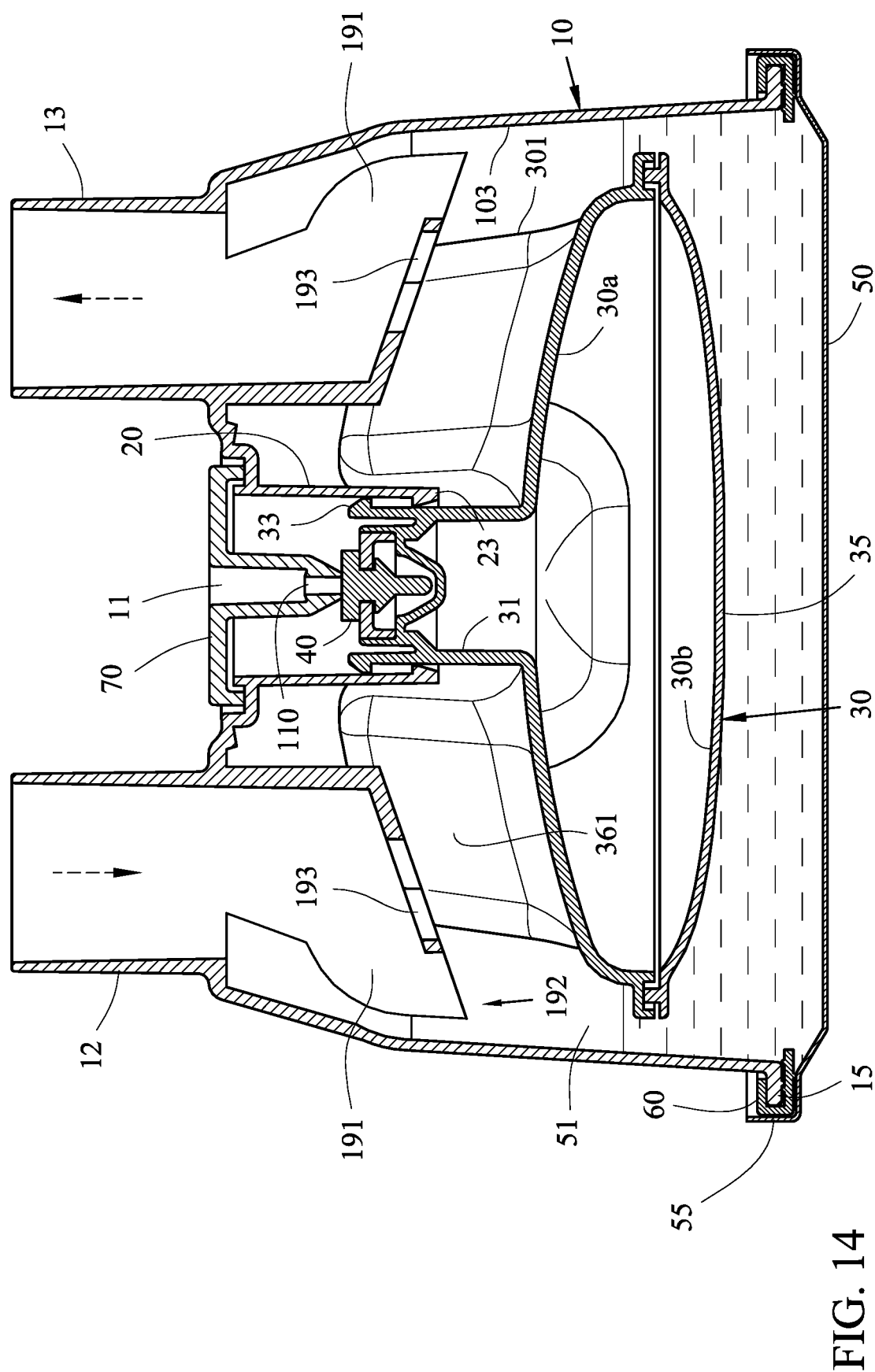
FIG. 14 is an operation diagram illustrating the first embodiment of the invention.

Referring to FIGS. 1 to 7, a humidification chamber structure in accordance with a first preferred embodiment of the invention comprises a shell body 10, an extending tube 20, a float 30, a sealing element 40 and a heated plate 50; the shell body 10 has a water inlet 11, a gas inlet 12 and a gas outlet 13, the inside of the shell body 10 is provided with a plurality of passage spacer plates 16; the extending tube 20 is integrally formed on the inside of the shell body 10, the position of the extending tube 20 corresponds to the water inlet 11, the extending tube 20 has a plurality of positioning blocks 23; the float 30 is a hollow container, the float 30 is provided with a plurality of concave portions 36, the central portion of the float 30 has an extending portion 31 (for example, but not limit to, the plurality concave portions 36 are distributed on the same side of the float 30, and the plurality concave portions 36 are annularly disposed on the extending portion 31), a top end 311 of the extending portion 31 has a plurality of hooks 33; the sealing element 40 can be disposed on the top end 311 of the extending portion 31, and the sealing element 40 is located below the water inlet 11; the heated plate 50 is located below the shell body 10, and the heated plate 50 is used for sealing the shell body 10 to form a chamber space 51 (Please also refer to FIG. 12); wherein the extending portion 31 of the float 30 can partially insert into the extending tube 20, the extending portion 31 can be suspended on the extending tube 20 by the plurality hooks 33 and the plurality positioning blocks 23, therefore a distance can be formed between and a bottom 35 of the float 30 the heated plate 50; the passage spacer plates 16 partially enters into the concave portions 36, the passage spacer plates 16 and the concave portions 36 form at least two complicated gas passages A1 in the chamber space 51 (Please also refer to FIG. 10 and FIG. 11); the outside surface 301 of the float 30 and the wall surface 103 of the shell body 10 form at least two annular gas passages A2 in the chamber space 51 (Please also refer to FIG. 10 and FIG. 11); when the water level of the chamber space 51 enables the float 30 to rise up until the sealing element 40 blocks a water inlet hole 110 of the water inlet 11, the water inlet 11 will stop inputting a liquid; when the water level of the chamber space 51 enables the float 30 to fall down until the sealing element 40 leaves from the water inlet hole 110, the water inlet 11 will input the liquid again (Please also refer to FIG. 12 and FIG. 14).

Examples of the combination manner of the float 30 and the shell body 10 will be illustrated below, the float 30 is consisted of an upper casing 30a and a lower casing 30b, the extending portion 31 is located at the upper casing 30a, and the plurality concave portions 36 are symmetrically disposed on the upper casing 30a (for example, a plurality of hollow convex portions 361 are symmetrically disposed on the upper casing 30a, and each of the concave portions 36 is formed by the adjacent convex portions 361), and the plurality passage spacer plates 16 are symmetrically disposed in the shell body 10; therefore the assembly of the float 30 and the shell body 10 is provided with the foolproof effect. For example, but not limit to, when the float 30 rotates 90 degrees relative to the cover 10, the passage spacer plates 16 of the cover 10 will also partially enter into the concave portions 36 (because the plurality concave portions 36 are symmetrically disposed on the upper casing 30a, and the plurality passage spacer plates 16 are symmetrically disposed in the shell body 10); even when the float 30 rotates 180 degrees relative to the cover 10, the passage spacer plates 16 of the cover 10 will also partially enter into the concave portions 36 (because the plurality concave portions 36 are symmetrically disposed on the upper casing 30a, and the plurality passage spacer plates 16 are symmetrically disposed in the shell body 10); even when the float 30 rotates 270 degrees relative to the cover 10, the passage spacer plates 16 of the cover 10 will also partially enter into the concave portions 36 (because the plurality concave portions 36 are symmetrically disposed on the upper casing 30a, and the plurality passage spacer plates 16 are symmetrically disposed in the shell body 10).

Examples of the functions of the lower casing 30b will be illustrated below, the lower casing 30b can be a shallow dish structure to avoid an increase in height of the float 30, and as a result of the lower casing 30b is the shallow dish structure, the lower casing 30b will be provided with a larger cross-sectional area, therefore the buoyant force of the float 30 can be increased.

Referring to FIGS. 12 to 15, examples of the suspension manner of the float 30 will be illustrated below, the plurality hooks 33 surrounds on the outside of the sealing element 40, and each of the hooks 33 is connected to the top end 311 of the extending portion 31; each of the positioning blocks 23 blocks each of the hooks 33 to escape from the extending tube 20, the float 30 can be suspended on the extending tube 20, therefore the bottom 35 of the float 30 will not contact the heated plate 50.

Figure 13:
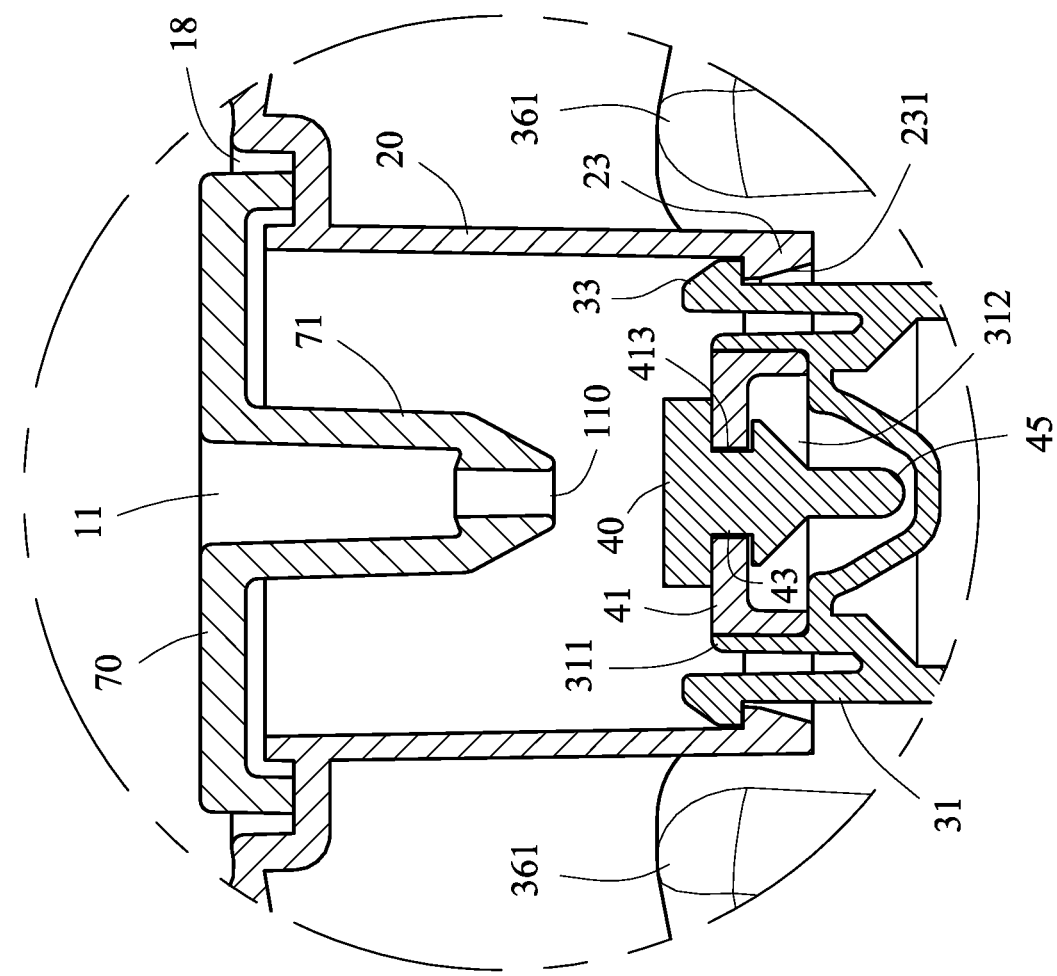
FIG. 13 is a partial enlarged view of the FIG. 12.
Figure 15:
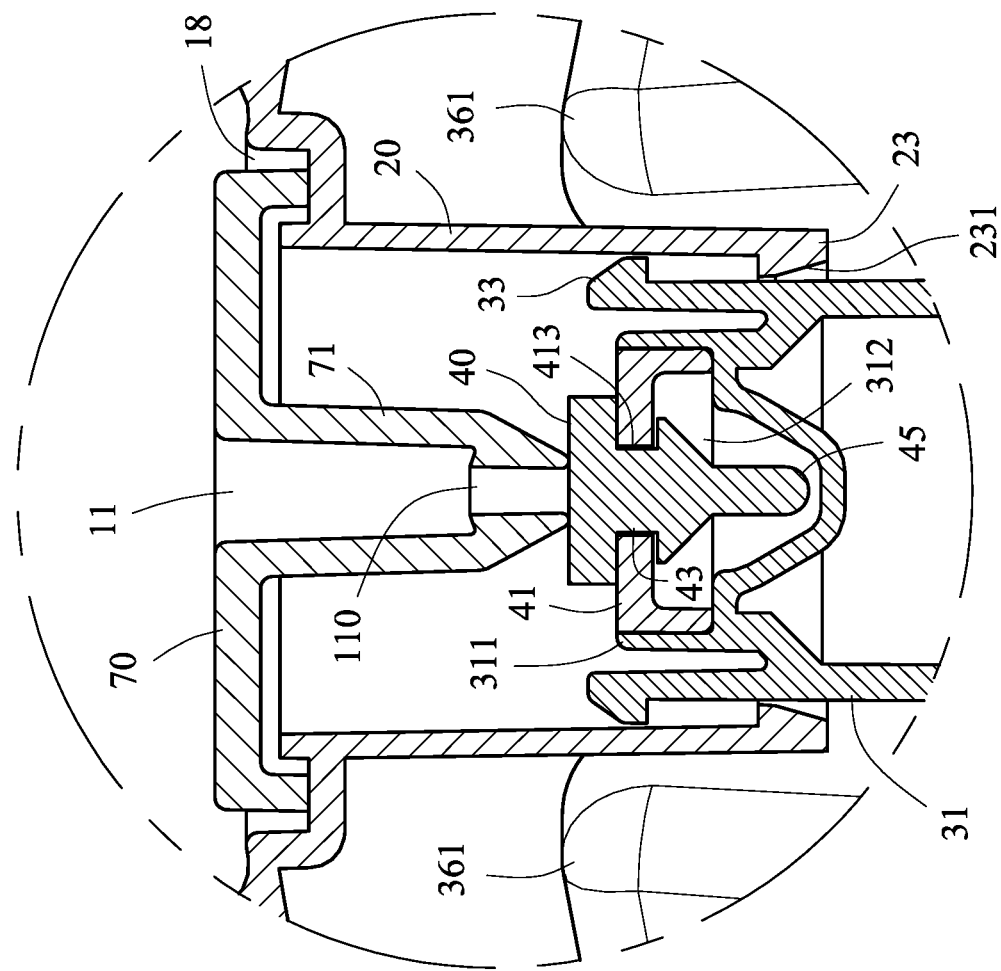
FIG. 15 is a partial enlarged view of the FIG. 14.

Examples of the combination manner of the extending portion 31 and the extending tube 20 will be illustrated below, each positioning block 23 further has an inclined surface 231; when the extending portion 31 of the float 30 inserts into the extending tube 20, each hooks 33 can use the inclined surface 231 of the positioning block 23 to easily insert into the extending tube 20 (as shown in FIG. 13 and FIG. 15).

Examples of the combination manner of the sealing element 40 and the float 30 will be illustrated below, the top end 311 of the extending portion 31 has a recess 312, the recess 312 can be provided with a fixing seat 41, the sealing element 40 can use the fixing seat 41 to fix on the top end 311 of the extending portion 31; wherein the sealing element 40 can be made from the silicone material, the sealing element 40 has a neck portion 43 and a pin 45, the neck portion 43 can be fixed in a fixing hole 413 of the fixing seat 41, and the pin 45 can be received in the recess 312 (as shown in FIG. 13 and FIG. 15).

Referring to FIGS. 3, 12 to 15, examples of the structure of the shell body 10 will be illustrated below, the shell body 10 has an annular groove 18, the annular groove 18 is connected with the extending tube 20 of the shell body 10; an upper cover 70 can be embedded on the annular groove 18, the water inlet 11 and the water inlet hole 110 are disposed on the upper cover 70, the water inlet hole 110 is located in the extending tube 20 (for example, the water inlet hole 110 is disposed in an extending post 71 of the upper cover 70, therefore the water inlet hole 110 can be located in the extending tube 20); thereby, the mold of the shell body 10 is easy to manufacture, the injection molding of the shell body 10 and the upper cover 70 will be easy for manufacturer.

Referring to FIGS. 8, 9, 12 and 14, examples of the additional structure of the shell body 10 will be illustrated below, the gas inlet 12 and the gas outlet 13 are respectively connected with a U-shaped spacer plate 19, each U-shaped spacer plate 19 is connected to an inclined plate 191, a notch 192 is formed between each inclined plate 191 and the wall surface 103 of the shell body 10, each inclined plate 191 has a through hole 193, an airflow can be allowed to pass through each notch 192 and each through hole 193; when the airflow enters into the gas inlet 12, the inclined plate 191 and the U-shaped spacer plate 19 connected with the gas inlet 12 can concentrate the airflow, therefore the airflow enters into the chamber space 51 by the notch 192 and the through hole 193, and the airflow can be properly buffered.

Examples of the structure evolution of the shell body 10 will be illustrated below, each U-shaped spacer plate 19 and each inclined plate 191 can partially protrude into at least one concave portion 36 of the float 30; wherein the U-shaped spacer plate 19 of the gas inlet 12 and the U-shaped spacer plate 19 of the gas outlet 13 are symmetrically disposed in the shell body 10, the plurality recesses 36 are symmetrically disposed on the float 30, and the plurality passage spacer plates 16 are symmetrically disposed in the shell body 10; therefore the assembly of the float 30 and the shell body 10 is provided with the foolproof effect.

Figure 1:
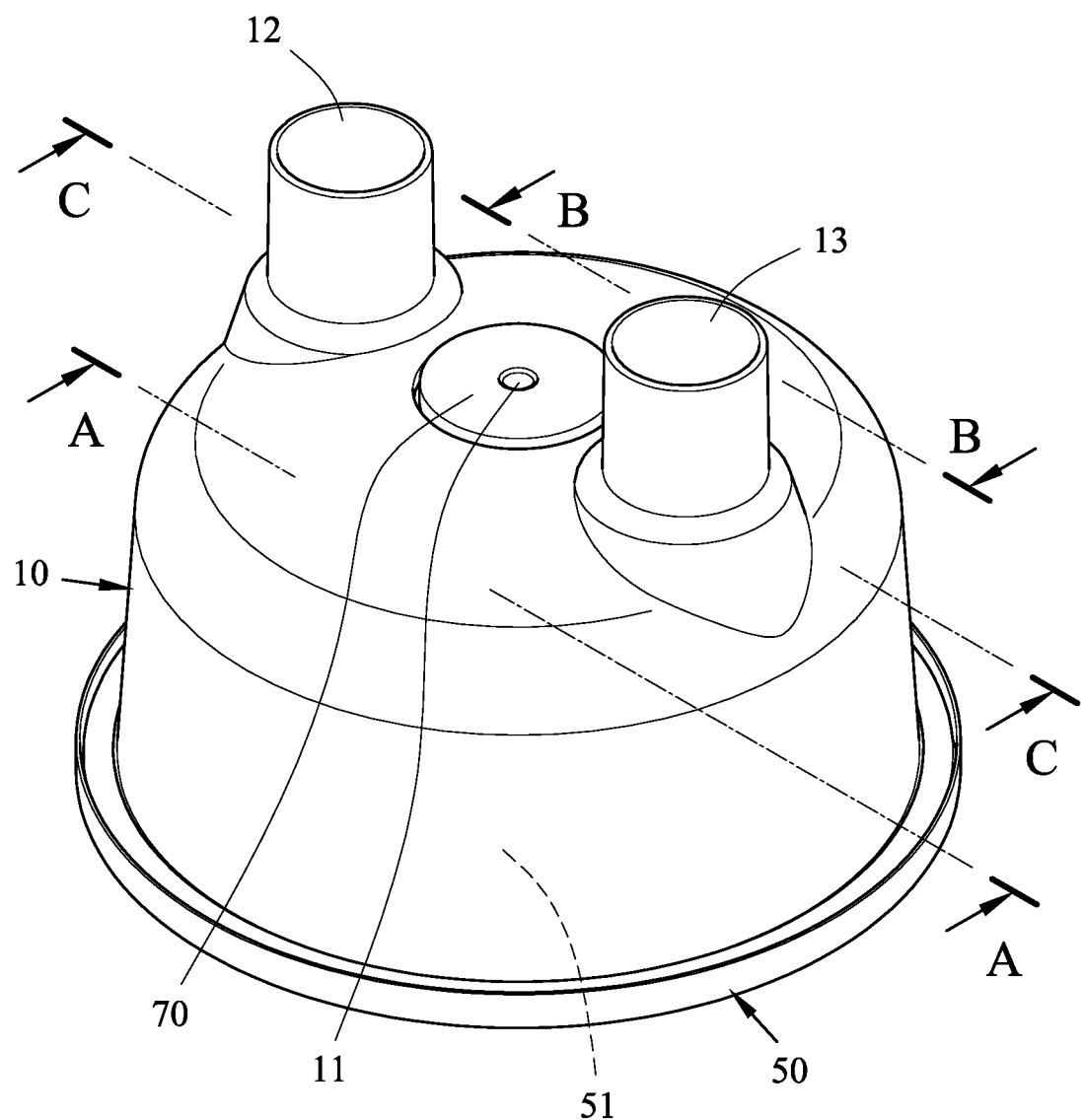
FIG. 1 is a perspective view showing a first preferred embodiment of the invention.
Figure 2:
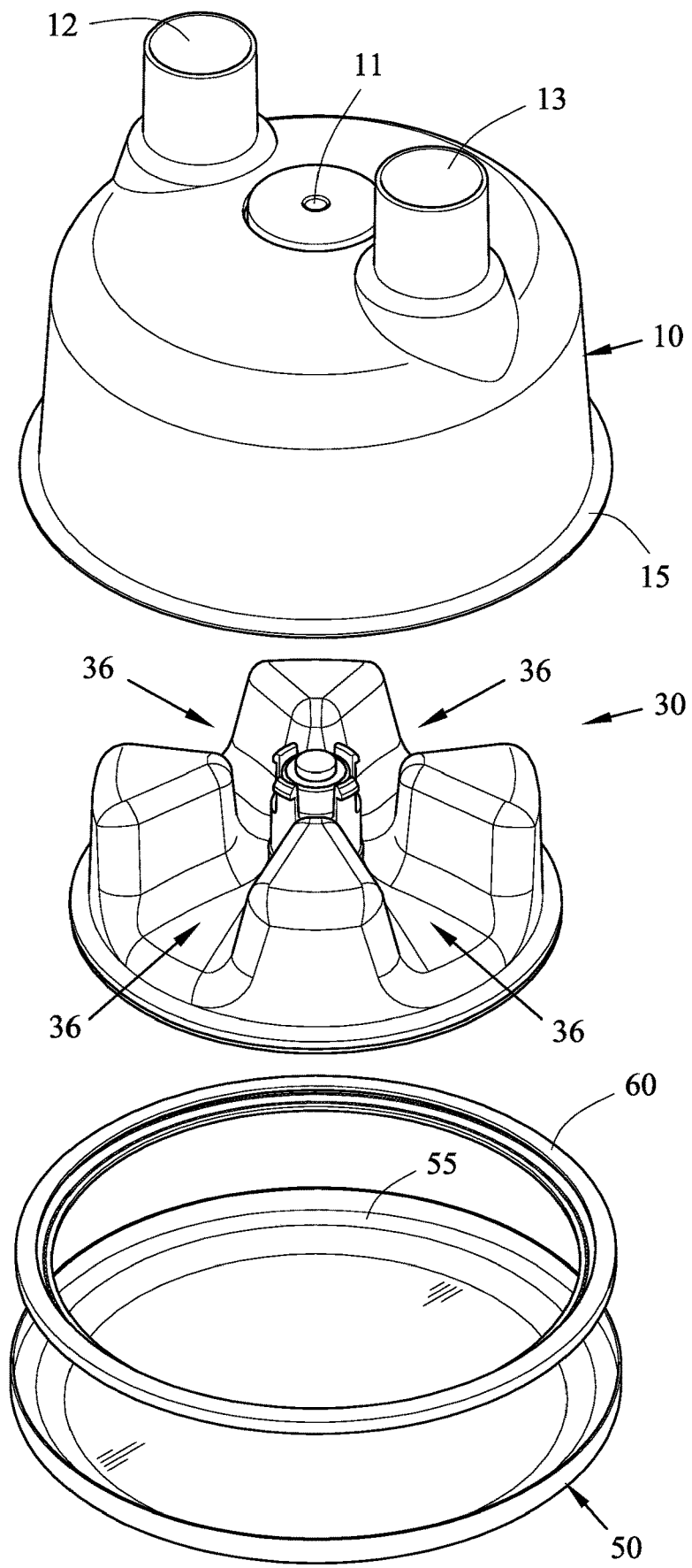
FIG. 2 is a partial exploded view showing the first preferred embodiment of the invention.
Figure 3:
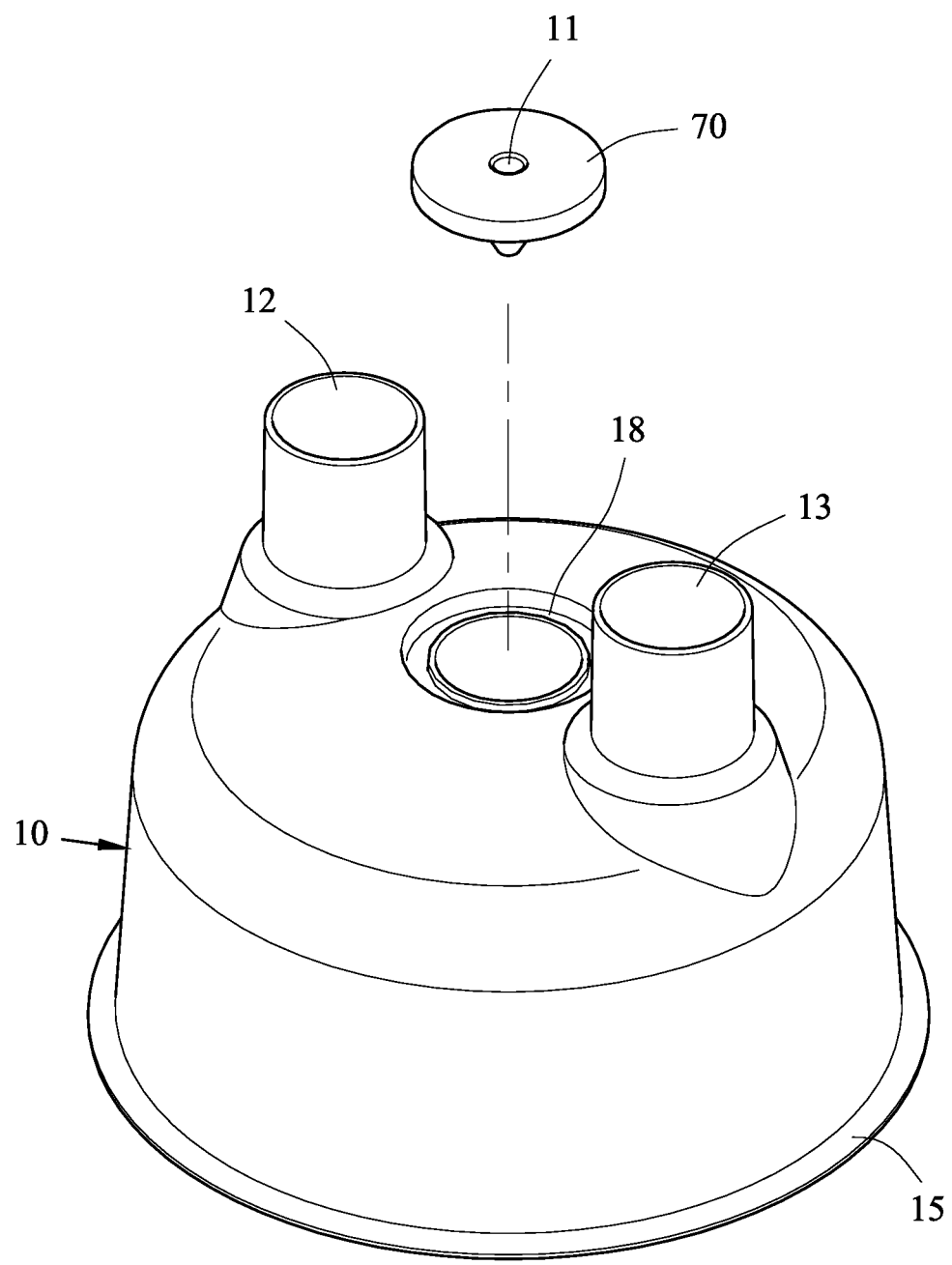
FIG. 3 is an exploded view showing the shell body and the upper cover of the invention.
Figure 4:
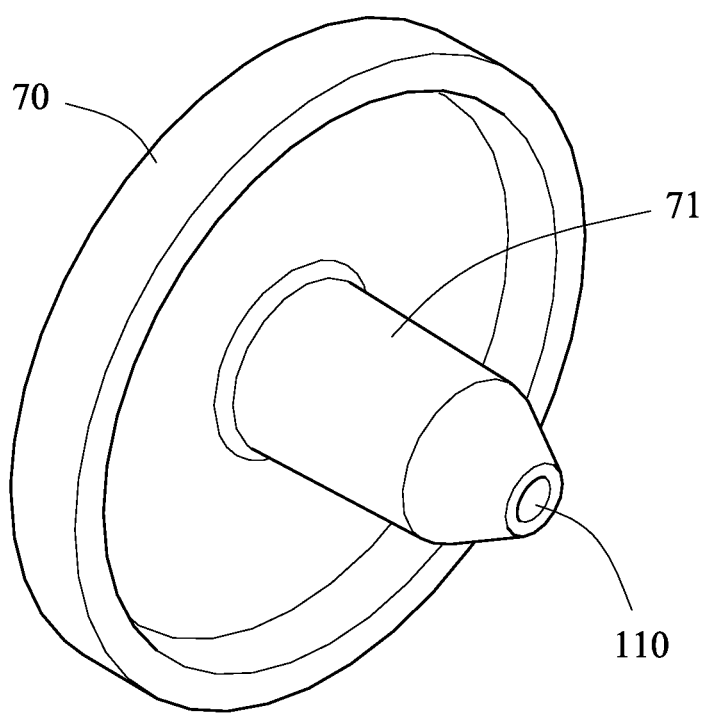
FIG. 4 is a perspective view showing the upper cover of the invention.
Figure 5:
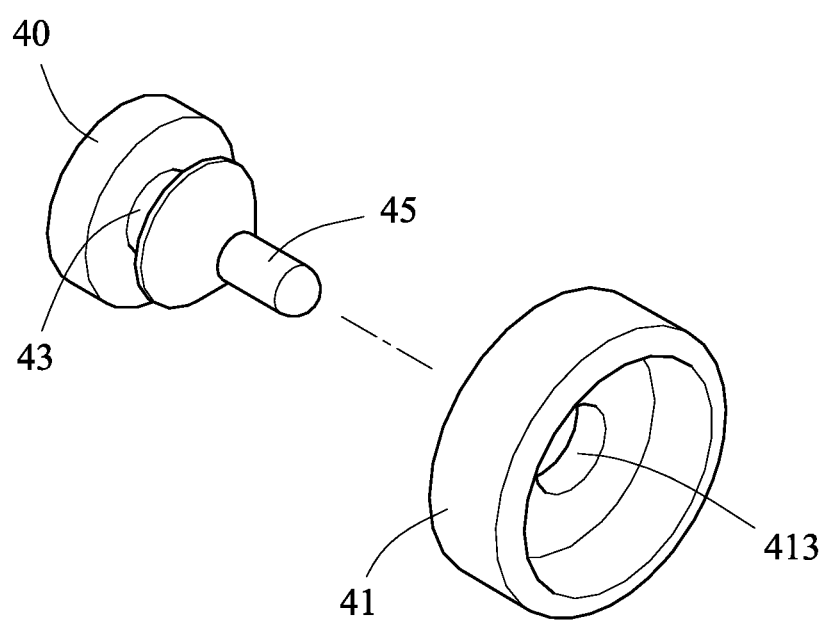
FIG. 5 is an exploded view showing the sealing element and the fixing seat of the invention.
Figure 6:
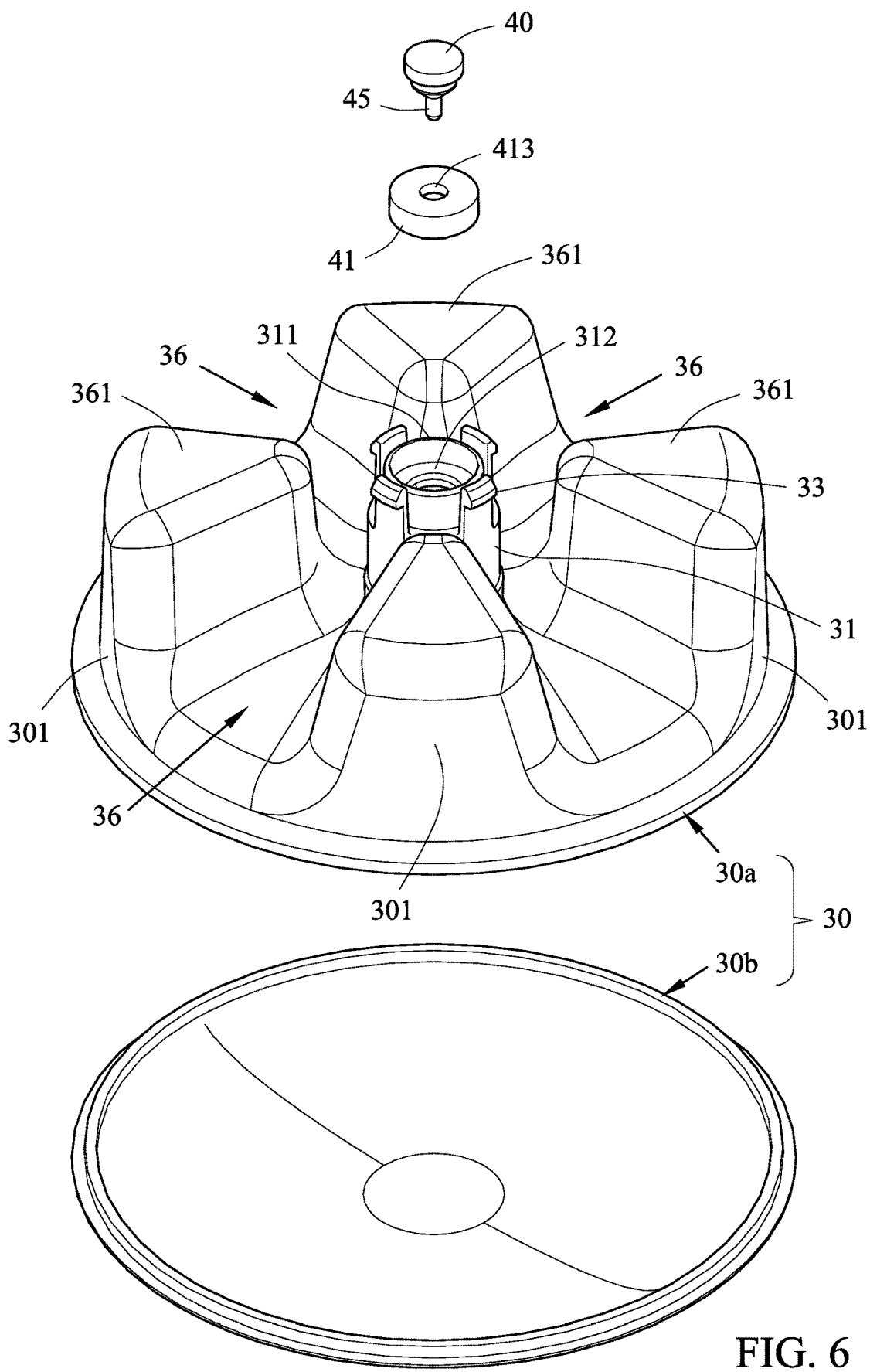
FIG. 6 is an exploded view showing the float, the sealing element and the fixing seat of the invention.
Figure 7:
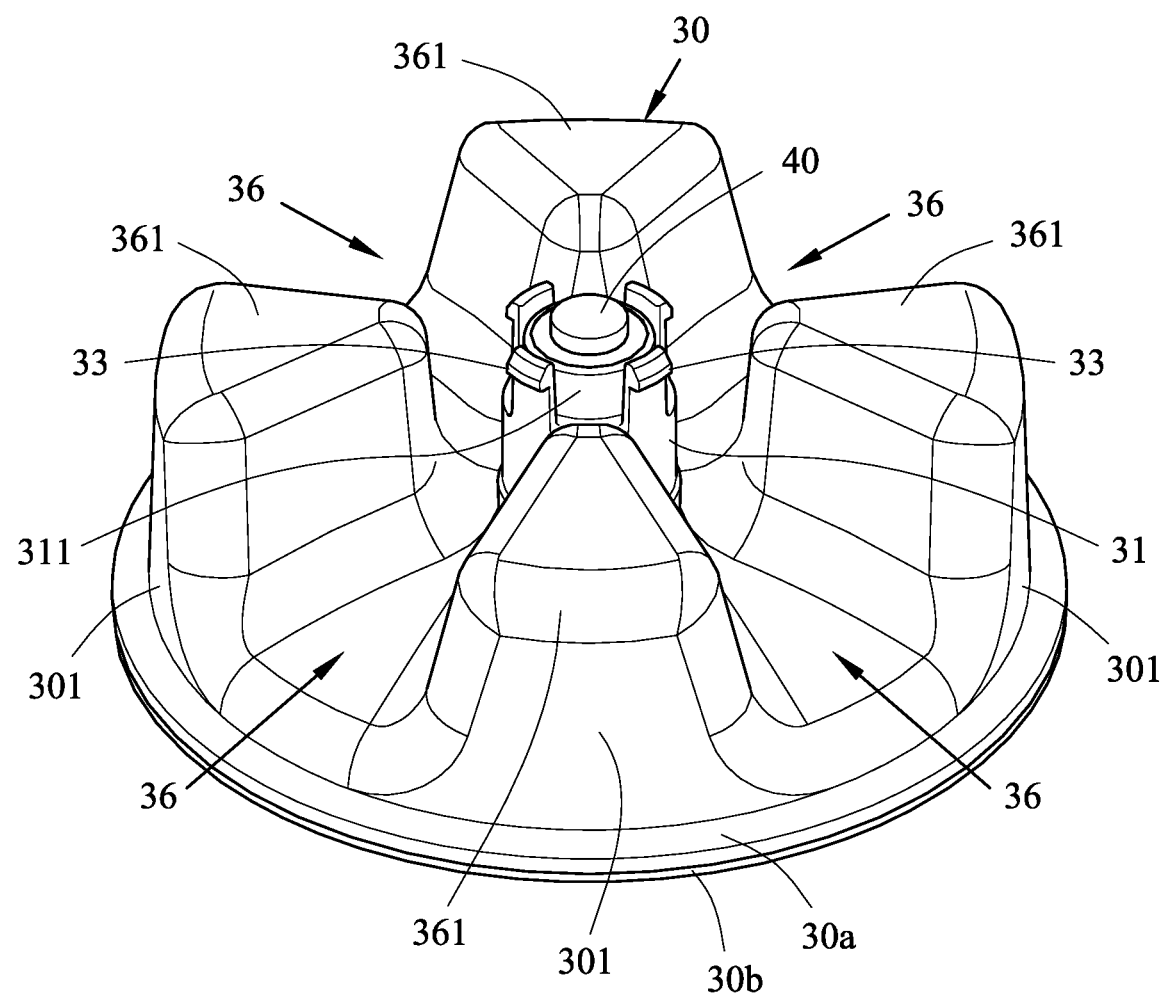
FIG. 7 is a perspective view showing the combination of the float, the sealing element and the fixing seat of the invention.
Figure 8:
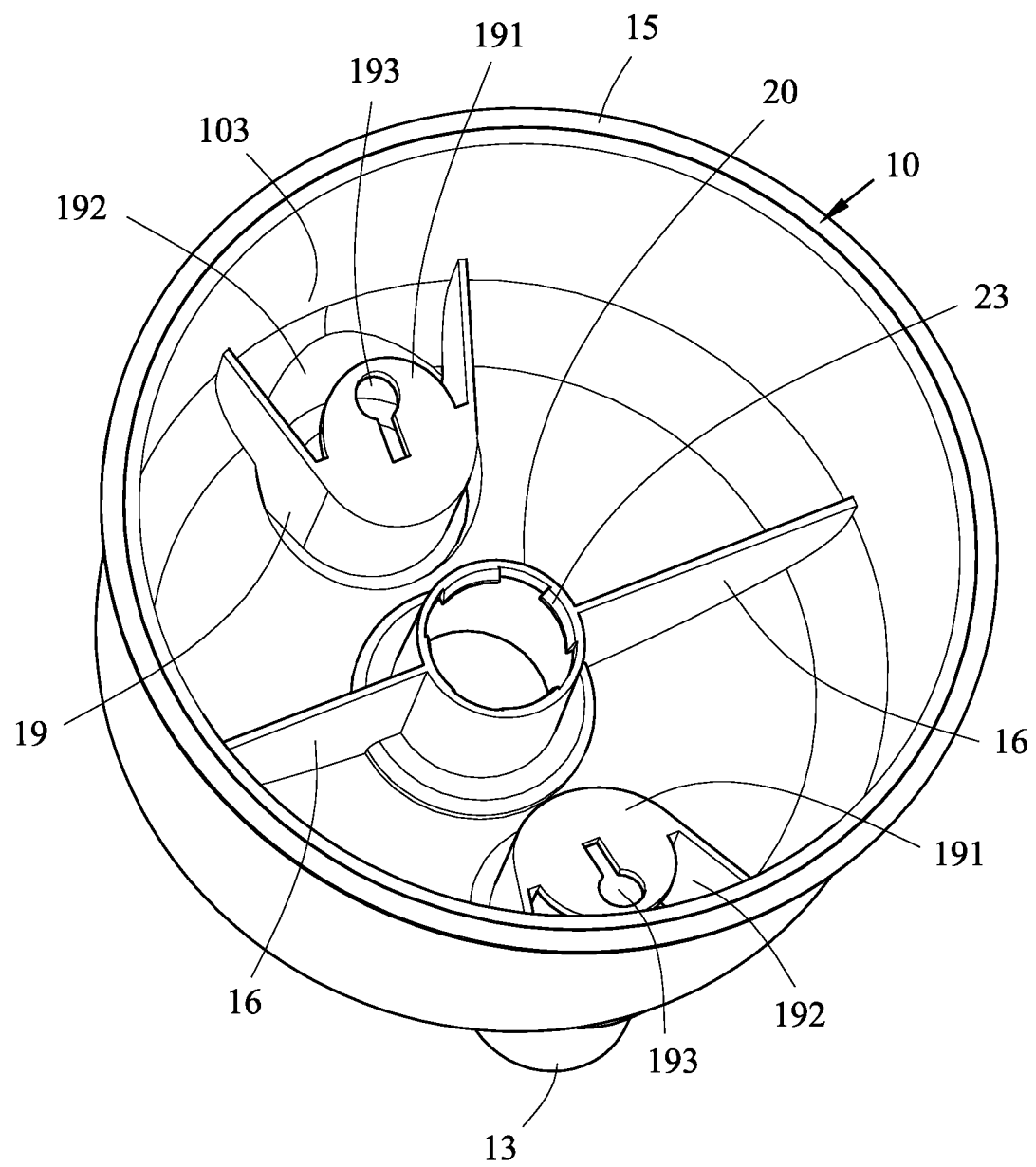
FIG. 8 and FIG. 9 are another perspective view showing the shell body of the invention.

Referring to FIGS. 2 and 12, examples of the sealing manner of the heated plate 50 and the shell body 10 will be illustrated below, the shell body 10 has an annular edge 15, the annular edge 15 is sealed with an edge 55 of the heated plate 50, a sealing ring 60 is disposed between the annular edge 15 and the edge 55 of the heated plate 50; wherein the sealing ring 60 can be wrapped on the annular edge 15.

Figure 9:
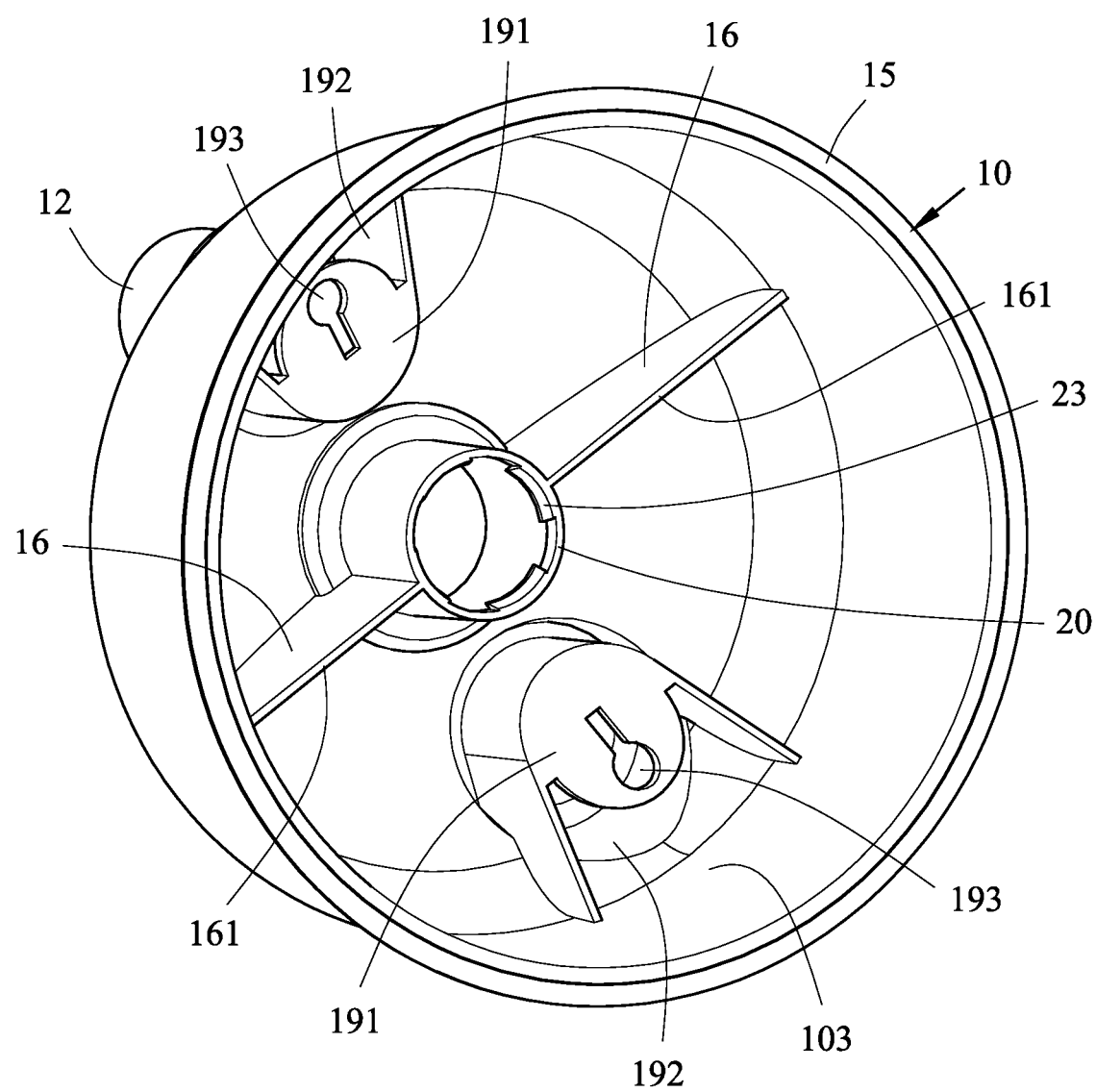
Figure 16:
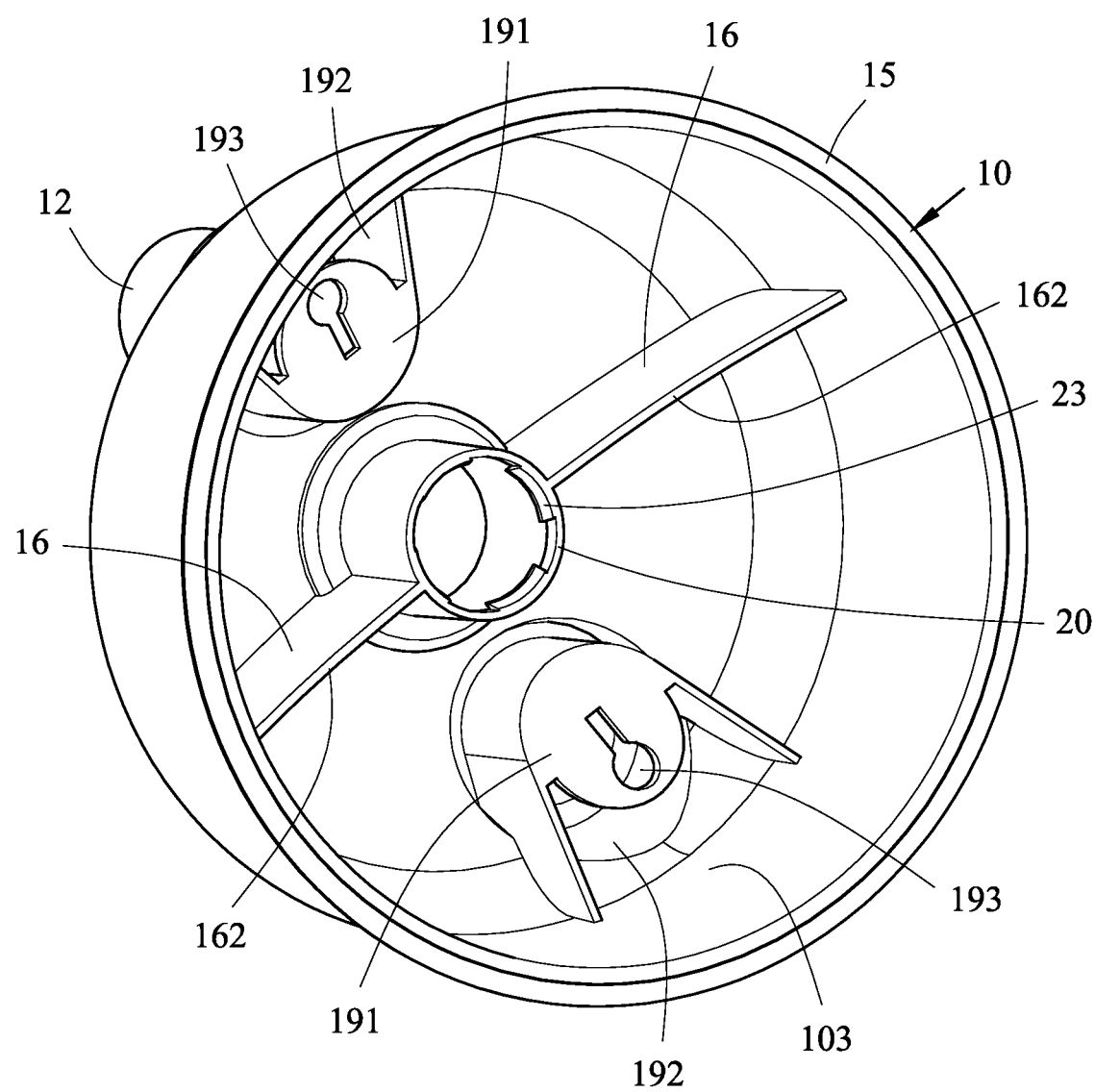
FIG. 16 is a perspective view showing the shell body of second preferred embodiment of the invention.

Referring to FIGS. 9 and 16, in the first embodiment, the plurality passage spacer plates 16 have a straight edge 161 (as shown in FIG. 9); in the second embodiment, the plurality passage spacer plates 16 have a curved edge 162 (as shown in FIG. 16); thereby forming different airflow impedances.

What is claimed is:

1. An auto feed humidification chamber with improved structure, the humidification chamber comprising:
a shell body (10), the shell body (10) has a water inlet (11), a gas inlet (12) and a gas outlet (13), the inside of the shell body (10) is provided with a plurality of passage spacer plates (16);
an extending tube (20), the extending tube (20) is integrally formed on the inside of the shell body (10), the position of the extending tube (20) corresponds to the water inlet (11), the extending tube (20) has a plurality of positioning blocks (23);
a float (30), the float (30) is a hollow container, the float (30) is provided with a plurality of concave portions (36), the central portion of the float (30) has an extending portion (31), a top end (311) of the extending portion (31) has a plurality of hooks (33);
a sealing element (40), the sealing element (40) is disposed on the top end (311) of the extending portion (31), and the sealing element (40) is located below the water inlet (11);
a heated plate (50), the heated plate (50) is located below the shell body (10), and the heated plate (50) is used for sealing the shell body (10) to form a chamber space (51);
wherein the extending portion (31) of the float (30) is configured to partially insert into the extending tube (20), the extending portion (31) is suspended on the extending tube (20) by the plurality of hooks (33) and the plurality of positioning blocks (23), therefore a distance is formed between a bottom of the float (30) and the heated plate (50); the passage spacer plates (16) and the concave portions (36) form at least two complicated gas passages (A1) in the chamber space (51);
an outside surface (301) of the float (30) and a wall surface (103) of the shell body (10) form at least two annular gas passages (A2) in the chamber space (51);
when the water level of the chamber space (51) enables the float (30) to rise up until the sealing element (40) blocks a water inlet hole (110) of the water inlet (11), the water inlet (11) will stop inputting a liquid; when the water level of the chamber space (51) enables the float (30) to fall down until the sealing element (40) leaves from the water inlet hole (110), the water inlet (11) will input the liquid again.

2. The auto feed humidification chamber with improved structure of claim 1, wherein the float (30) is consisted of an upper casing (30a) and a lower casing (30b), the extending portion (31) is located at the upper casing (30a), and the plurality concave portions (36) are symmetrically disposed on the upper casing (30a), and the plurality passage spacer plates (16) are symmetrically disposed in the shell body (10); therefore the assembly of the float (30) and the shell body (10) is provided with a foolproof effect.

3. The auto feed humidification chamber with improved structure of claim 1, wherein the plurality of hooks (33) surround the outside of the sealing element (40), and each of the hooks (33) is connected to the top end (311) of the extending portion (31); each of the positioning blocks (23) blocks each of the hooks (33) to escape from the extending tube (20), therefore the float (30) is suspended on the extending tube (20), and therefore the bottom (35) of the float (30) will not contact the heated plate (50).

4. The auto feed humidification chamber with improved structure of claim 1, wherein each positioning block (23) further has an inclined surface (231); when the extending portion (31) of the float (30) inserts into the extending tube (20), each hook (33) is configured to easily insert into the extending tube (20) by the inclined surface (231) of the positioning block (23).

5. The auto feed humidification chamber with improved structure of claim 1, wherein the top end (311) of the extending portion (31) has a recess (312), the recess (312) is provided with a fixing seat (41), the sealing element (40) is configured to fix on the top end (311) of the extending portion (31) by the fixing seat (41).

6. The auto feed humidification chamber with improved structure of claim 5, wherein the sealing element (40) is made from the a silicone material, the sealing element (40) has a neck portion (43) and a pin (45), the neck portion (43) is fixed in a fixing hole (413) of the fixing seat (41), and the pin (45) is received in the recess (312).

7. The auto feed humidification chamber with improved structure of claim 1, wherein the shell body (10) has an annular groove (18), the annular groove (18) is connected with the extending tube (20) of the shell body (10);

an upper cover (70) is embedded on the annular groove (18), the water inlet (11) and the water inlet hole (110) are disposed on the upper cover (70), the water inlet hole (110) is located in the extending tube (20).

8. The auto feed humidification chamber with improved structure of claim 1, wherein the gas inlet (12) and the gas outlet (13) are respectively connected with a U-shaped spacer plate (19), each U-shaped spacer plate (19) is connected to an inclined plate (191), a notch (192) is formed between each inclined plate (191) and the wall surface (103) of the shell body (10), each inclined plate (191) has a through hole (193), an airflow is allowed to pass through each notch (192) and each through hole (193), each U-shaped spacer plate (19) and each inclined plate (191) is configured to partially protrude into at least one concave portion (36) of the float (30).

9. The auto feed humidification chamber with improved structure of claim 8, wherein the U-shaped spacer plate (19) of the gas inlet (12) and the U-shaped spacer plate (19) of the gas outlet (13) are symmetrically disposed in the shell body (10), the plurality of recesses (36) are symmetrically disposed on the float (30), and the plurality of passage spacer plates (16) are symmetrically disposed in the shell body (10); therefore the assembly of the float (30) and the shell body (10) is provided with a foolproof effect.

10. The auto feed humidification chamber with improved structure of claim 1, wherein each of the passage spacer plates (16) has a straight edge (161) or a curved edge (162).

11. An auto feed humidification chamber with improved structure, the humidification chamber has a float (30) which is a hollow container, the float (30) comprising:

an extending portion (31) disposed at a central portion of the float (30);

a plurality of hooks (33) disposed at a top end (311) of the extending portion (31);

a plurality of concave portions (36), the plurality concave portions (36) are annularly disposed on the extending portion (31);

a sealing element (40), the sealing element (40) is configured to fix on the top end (311) of the extending portion (31);

wherein the float (30) is configured to suspend in a chamber space (51) of the humidification chamber by the hooks (33), the plurality concave portions (36) is configured to form at least two complicated gas passages (A1) in the chamber space (51), an outside surface (301) of the float (30) is configured to form at least two annular gas passages (A2) in the chamber space (51); wherein the float (30) is consisted of an upper casing (30a) and a lower casing (30b), the extending portion (31) is located at the upper casing (30a), and the plurality of concave portions (36) are disposed on the upper casing (30a); wherein the float (30) has a plurality of hollow convex portions (361), the hollow convex portions (361) are disposed on the upper casing (30a), and each of the concave portions (36) is formed by the adjacent convex portions (361); wherein the plurality of recesses (36) are symmetrically disposed on the upper casing (30a), therefore the assembly of the float (30) is provided with a foolproof effect.

12. The auto feed humidification chamber with improved structure of claim 11, wherein the lower casing (30b) is a shallow dish structure.

13. The auto feed humidification chamber with improved structure of claim 11, wherein the hollow convex portions (361) are symmetrically disposed on the upper casing (30a).

14. The auto feed humidification chamber with improved structure of claim 11, wherein the plurality of hooks (33) are annularly disposed on the extending portion (31) on the outside of the sealing element (40), and each of the hooks (33) is connected to the top end (311) of the extending portion (31).

15. The auto feed humidification chamber with improved structure of claim 11, wherein the top end (311) of the extending portion (31) has a recess (312), the recess (312) is provided with a fixing seat (41), the sealing element (40) is configured to fix on the top end (311) of the extending portion (31) by the fixing seat (41).

16. The auto feed humidification chamber with improved structure of claim 15, wherein the sealing element (40) is made from a silicone material, the sealing element (40) has a neck portion (43) and a pin (45), the neck portion (43) is fixed in a fixing hole (413) of the fixing seat (41), and the pin (45) is received in the recess (312).

* * * * *